(12) United States Patent
Lien et al.

(10) Patent No.: US 10,668,122 B2
(45) Date of Patent: Jun. 2, 2020

(54) **EXTRACT OF *TOONA SINENSIS* FROM SUPERCRITICAL FLUID EXTRACTION FOR TREATING DIABETES AND METABOLIC DISEASE, THE PREPARATION METHOD AND THE USE THEREOF**

(71) Applicants: Metal Industries Research & Development Centre, Kaohsiung (TW); Kaohsiung Medical University, Kaohsiung (TW)

(72) Inventors: Pei-Jung Lien, Taipei (TW); Chuan-Chia Sun, Kaohsiung County (TW); Tzu-Chen Kuo, Kaohsiung (TW); Sheng-Chung Yang, Kaohsiung (TW); Yang-Chang Wu, Kaohsiung (TW); Fang-Rong Chang, Kaohsiung (TW); Tusty-Jiuan Hsieh, Kaohsiung (TW); Yi-Hong Tsai, Kaohsiung (TW); Ying-Chi Du, Chiayi (TW)

(73) Assignees: METAL INDUSTRIES RESEARCH & DEVELOPMENT CENTRE, Kaohsiung (TW); KAOHSIUNG MEDICAL UNIVERSITY, Kaohsiung (TW)

( * ) Notice: Subject to any disclaimer, the term of this patent is extended or adjusted under 35 U.S.C. 154(b) by 153 days.

(21) Appl. No.: 15/596,799

(22) Filed: May 16, 2017

(65) Prior Publication Data
US 2017/0252393 A1 Sep. 7, 2017

Related U.S. Application Data

(63) Continuation of application No. 12/979,641, filed on Dec. 28, 2010, now abandoned.

(30) Foreign Application Priority Data

Dec. 30, 2009 (TW) ................ 098145982 A (51) Int. Cl.
*A61K 36/58* (2006.01)
*A61K 36/00* (2006.01)
*A23L 33/105* (2016.01)

(52) U.S. Cl.
CPC ............ *A61K 36/58* (2013.01); *A23L 33/105* (2016.08)

(58) Field of Classification Search
None
See application file for complete search history.

(56) References Cited

U.S. PATENT DOCUMENTS 5,017,397 A * 5/1991 Nguyen ............... A23L 3/3472
426/489
6,232,506 B1 * 5/2001 Kido ................... C07C 29/172
568/383

2005/0175716 A1 * 8/2005 Lee ....................... A61K 36/23
424/725
2008/0095719 A1 4/2008 Herrmann et al.
2009/0169658 A1 7/2009 Ho et al.

FOREIGN PATENT DOCUMENTS

| CN | 101406487 A | 4/2009 |
| WO | 2007070355 A2 | 6/2007 |

OTHER PUBLICATIONS

Marco (Supercritical fluid extraction and fractionation of natural matter, J. Supercritical Fluids 38 (2006), pp. 146-166) (Year: 2006).*
Mu et al. (Rapid Determination of Volatile Compounds in Toona sinensis by MAE-HS-SPME, Chromatographia, vol. 65, No. 7/8, pp. 463-467, 2007, pp. 463-465) (Year: 2007).*
Chen, H.M., Wu, Y.C., Chia, Y.C., Chang, F.R., Hsu, H.K., Hsieh, Y.C., Chen, C.C., Yuan, S.S. Gallic acid, a major component of Toona sinensis leaf extracts, contains a ROS-mediated anti-cancer activity in human prostate cancer cells. Cancer Lett. 2009, 286(2): 161-71.
Chang, H.L., Hsu, H.K., Su, J.H., Wang, P.H., Chung, Y.F., Chia, Y.C., Tsai, L.Y., Wu, Y.C., Yuan, S.S.F. The fractionated Toona sinensis leaf extract induces apoptosis of human ovarian cancer cells and inhibits tumor growth in a murine xenograft model. Gynecol. Oncol. 2006, 102(2): 309-14.
Wang, P.H., Tsai, M.J., Hsu, C.Y., Wang, C.Y., Hsu, H.K., Weng, C.F. Toona sinensis Roem (*Meliaceae*) leaf extract alleviates hyperglycemia via altering adipose glucose transporter 4. Food Chem. Toxicol. 2008, 46(7): 2554-60.
Wang, J.S., Sheaff, C.N., Yoon, B., Addleman, R.S., Wai, C.M. Extraction of uranium from aqueous solutions by using ionic liquid and supercritical carbon dioxide in conjunction. Chem. Eur. J. 2009, 15(17): 4458-63.
Michielin, E.M.Z., Salvador, A.A., Riehl, C.A.S., Smania Jr., A., Ferreira, S.R.S. Chemical composition and antibacterial activity of Cordia verbenacea extracts obtained by different methods. Bioresour. Technol. 2009, 100(24): 6615-23.
Yamaguchi, K., Murakami, M., Nakano, H., Konosu, S., Kokura, T.,Yamamoto, H., Kosaka, M., Hata, K. Supercritical carbon dioxide extraction of oils from Antarctic krill. J. Agric. Food Chem. 1986, 34(5): 904-7.

(Continued)

*Primary Examiner* — Michael Barker
*Assistant Examiner* — Randall Winston
(74) *Attorney, Agent, or Firm* — Volpe and Koenig, P.C.

(57) ABSTRACT

The *Toona sinensis* extract of the present invention is prepared using supercritical fluid technique, wherein the method includes steps of: (a) drying the leaves of *T. sinensis*; (b) pulverizing the leaves as particles; and (c) extracting the particles with supercritical carbon dioxide to obtain the *T. sinensis* extract. This supercritical *T. sinensis* extract not only can decrease blood sugar level, but also promotes lipid degradation, inhibits the formation of huge lipid droplet and improves the metabolic symptoms. Accordingly, the *T. sinensis* extract further is able to be prepared as food supplement and pharmaceuticals.

10 Claims, 8 Drawing Sheets

(56) References Cited

OTHER PUBLICATIONS

Wang, L., Weller, C.L. Schlegel, V.L., Carr, T.P. Cuppeff, S.L. Supercritical CO2 extraction of lipids from grain sorghum dried distillers grains with solubles. Bioresour. Technol. 2008, 9(5): 1373-82.
Ronyai, E., Simandi, B., Tomoskozi, S., Deak, A., Vigh, L., Weinbrenner, Z. Supercritical fluid extraction of corn germ with carbon dioxide-ethyl alcohol mixture. J. Supercrit. Fluids, 1998, 14(1): 75-81.
Watson, R.T., Pessin J.E., GLUT4 translocation: the last 200 nanometers. Cell. Signal. 2007, 19(11): 2209-17.
Kinkel, A.D., Fernyhough, M.E., Helterline, D.L., Vierck, J.L., Oberg, K.S., Vance, T.J., Hausman, G.J., Hill, R.A., Dodson, M.V. Oil red-O stains non adipogenic cells: a precautionary note. Cytotechnol. 2004, 46(1): 49-56.
Liao, J.W., Chung, Y.C., Yeh, J.Y., Lin, Y.C., Lin, Y.G., Wu, S.M., Chan, Y.C. Safety evaluation of water extracts of Toona sinensis Roemor leaf. Food Chem. Toxicol. 2007, 45(8): 1393-99.
Hsieh, C.L., Lin, Y.C., Ko, W.S., Peng, C.H., Huang, C.N., Peng, R.Y. Inhibitory effect of some selected nutraceutic herbs on LDL glycation induced by glucose and glyoxal. J. Ethnopharmacol. 2005, 102(3): 357-363.
Yang, Y.C. Hsu, H.K. Hwang, J.H., Hong, S.J. Enhancement of glucose uptake in 3T3-L1 adipocytes by Toona sinensis leaf extract. Kaohsiung J. Med. Sci. 2003, 19(7): 327-32.
Kiess, W., Petzold, S., Topfer, M., Garten, A., Bluher, S., Kapellen, T., Korner, A., Kratzsch, J. Adipocytes and adipose tissue. Best Pract. Res. Clin. Endocrinol. Metab. 2008, 22(1): 135-53.
Chen, X.H., Zhao, Y.P., Xue, J., Ji, C.F., Gao, C.L., Zhu, J.G., Qin, D.N., Kou, C.Z., Qin, X.H., Tong, J.L., Guo, X.R. TNF-α induces mitochondrial dysfunction in 3T3-L1 adipocytes. Mol. Cell. Endocrinol. 2010, 328(1-2): 63-69.
Lishizhen Medicine and Material Medical Reasearch, Jone 2008, vol. 19, Issue 6, pp. 1429-1430.
Zhengzhou Tobacco Research Institute of CNTC, Feb. 2, 2005, 4.
Hsieh, Tusty-Jivan et al. "Anti-diabetic properties of non-polar Toona sinensis Roem extract prepared by supercritical-CO2 fluid"; Food and Chemical Toxicology, vol. 50, pp. 779-789 (2012) Elsevier Ltd.
Journal of Changzhi Medical College, 2008, 4(22): 315-317.
Journal of Chinese Medicinal Materials, 2008, 31(11):1712-1714.
Journal of Chinese Institute of Food Science and Technology, Issue 4, 2007, pp. 3-7.
Taiwanese Patent Application Office Action.
Wang Pei-Hwei, May-Jywan Tsai, Chia-Yu Hsu, Chia-Yi Wang, Hseng-Kuang Hsu, Ching-Feng Weng, "Toona sinensis Roem (*Meliaceae*) leaf extract alleviates hyperglycemia via altering adipose glucose transporter 4." Food and Chemical Toxicology 46 (2008) 2554-2560.
Hui-Chiu Chang, Wen-Chun Hung, Ming-Shyan Huang and Hseng-Kuang Hsu, "Extract from the Leaves of Toona sinensis Roemor Exerts Potent Antiproliferative Effect on Human Lung Cancer Cells." The American Journal of Chinese Medicine, vol. 30, Nos. 2 & 3, 307-314.
Chung-Jen Chen, Martin Michaelis, Hseng-Kuang Hsu, Chin-Chuan Tsai, Kunder D. Yang, Yang-Chang Wu, Jindrich Cinatl Jr., Hans Wilhelm Doerr, "Toona sinensis Roem tender leaf extract inhibits SARS coronavirus replication." Journal of Ethnopharmacology 120 (2008) 108-111.
Sabrina Fan, Huan-Nan Chen, Chen-Jhe Wang, Wei-Chung Tseng, Hseng-Kuang Hsu, Ching-Feng Weng, "Toona sinensis Roem (*Meliaceae*) leaf extract alleviates liver fibrosis via reducing TGFB1 and collagen." Food and Chemical Toxicology 45 (2007) 2228-2236.
Hsin-Ling Yang, Wen-Huei Chang, Yi-Chen Chia, Chin-Jung Huang, Fung-Jou Lu, Hseng-Kuang Hsu, You-Cheng Hseu, "Toona sinensis extracts induces apoptosis via reactive oxygen species in human premyelocytic leukemia cells." Food and Chemical Toxicology 44 (2006) 1978-1988.
Hai Feng, Haibin Ma, Huiying Lin and Ramesh Putheti, "Antifatigue activity of water extracts of Toona sinensis Roemor leaf and exercise-related changes in lipid peroxidation in endurance exercise." Journal of Medicinal Plants Research vol. 3(11), pp. 949-954, Nov. 2009.
Chen et al., "Extraction of Flavanoids from Toona sinensis (*A Juss*) Roem Leaves by Superficial CO2 Fluid." Fine Chemicals, vol. 24, No. 8, Aug. 2007.
Chinese Office Action in Chinese Application 201080060000.0 dated Jul. 29, 2013.
Mu et al. (Rapid Determination of Volatile Compounds in Toona sinensis by MAE-HS-SPME followed by GC-MS, Chomatographia, vol. 65, No. 7/8, pp. 463-467, 2007, pp. 463-465).
Hsieh et al., "Separation of Phenols from the Leaves of Toona Sinensis (*Meliaceae*) by Capillary Electrophoresis." Journal of the Chinese Chemical Society, vol. 53, pp. 1203-1208, 2006 (2006).
Kleiman et al., "Fatty Acid Composition of Seed Oils of the Meliaceae, Including One Genus Rich in cis-Vaccenic Acid." JAOCS, vol. 61, No. 12, pp. 1836-1838, Dec. 1984 (Dec. 1984).
Chen et al., "Extraction of Active Ingredient of Tonna sinensis (*A. Juss.*) Roem Sprouts by Supercritical CO2 and Microwave Combined Technique." Jingxi Huagong (Fine Chemicals), vol. 25, No. 10, pp. 961-965, Oct. 2008 (Oct. 2008).

\* cited by examiner

EXTRACT OF *TOONA SINENSIS* FROM SUPERCRITICAL FLUID EXTRACTION FOR TREATING DIABETES AND METABOLIC DISEASE, THE PREPARATION METHOD AND THE USE THEREOF

This application is a continuation of U.S. patent application Ser. No. 12/979,641, filed Dec. 28, 2010, which claims the benefit of Taiwan Patent Application No. 098145982, filed Dec. 30, 2009, both of which are incorporated by reference as if fully set forth.

FIELD OF THE INVENTION

The present invention relates to a *Toona sinensis* extract, in particular to an extract of *T. sinensis* supercritical fluid and the preparation method and the use thereof. The supercritical *T. sinensis* extract can improve the glucose absorption in vivo, improve the lipid degradation and block the formation of the huge lipid droplet, and thus can be developed as the preventive food, drinks or therapeutic reagents on the metabolic syndromes.

BACKGROUND OF THE INVENTION

*Toona sinensis* is a Meliaceae defolite arbor, and its leaves can be used in food and show the medicinal functions on antiphlogosis, detoxification, disinfestations and the treatments on enteritis, dysentery, carbuncle, scabies, tinea capitis, and the improvements on somatoplasm. In the folk healing in China, the root skin of *T. sinensis* can be used to treat leucorrhoea, rheumatism, and gastrointestinal disorders, and the water with leaves can wash away tinea. *T. sinensis* further shows functions on prevention of cold and enteritis.

Chen et al. (2009) indicated that gallic acid extracted from the leaves of *T. sinensis* has the reactive oxygen species (ROS)-mediated anti-tumor activity on prostate cancer, and the extraction of *T. sinensis* leaves is made by boiling *T. sinensis* leaves in the water, filtering through sieves, lyophilizing and extracting with ethanol with various concentrations and the lyophilization treatments to obtain different extracts (Chang et al., 2006; Wang et al., 2008). In addition, U.S. Patent Publication No. 2009/0169658 A1 also indicated that the extract is afforded by the water extraction on *T. sinensis* leaves and the alcohol processed water extract is further obtained using liquid chromatography with reverse column and is used to inhibit the proliferation of cancer cells. Some food advertisements exaggerate that the *T. sinensis* tea brewed with hot water on the *T. sinensis* tea bags has the anti-tumor effect. However, the temperature, vapor and pressure of hot water are not sufficient to leach the components of *T. sinensis* into the water, and the dosages of components also do not achieve the therapeutic dosage and the therapeutic concentration.

Water and various organic solvents have different polarities, and the extraction uses the strength/weakness of the distribution coefficients of chemicals to the organic solvents to obtain the target extract. Furthermore, partial extracts might be destroyed or lost by the water-boiling extraction or the organic-solvent extraction, which thus results in the decrease of yield and recovery. The remaining organic solvent in the extracts also might harm the users. Therefore, finding the extraction method with advantages of non-toxicity and non-residue and without decrease of yield/recovery becomes the target in the application of *T. sinensis*.

Obesity, diabetes mellitus and their derived metabolic diseases are the interesting issues along with the human culture progress, and obesity is the main reason for the diseases such as cardiovascular disease, insulin resistance, diabetes mellitus and cancer, etc. The currently effective manner to decrease blood glucose is the subcutaneous injection of insulin. However, it needs to tightly monitor blood glucose and adjust insulin dosage, and thus it makes the diabetes patients' lives inconvenient. Type II diabetes mainly is treated with oral hypoglycemic agents, which mainly includes four groups, insulin-secreting agents (sulfonylureas and glinides), Metformin, insulin sensitizer (such as thiazolidinedion (TZD)) and α-glucosidase inhibitor. The functional mechanism and side effects in each group are not the same, and patients must try several drugs to find out the sufficient and effective drugs.

Since some oral hypoglycemic agents would induce gastrointestinal side effects such as diarrhea to result in patients' repulsion, they cannot be taken by the patients with liver or kidney disfunction. Further, rosiglitazone of the insulin sensitizer-typed drugs has hazard on increasing myocardial infarction and fracture in women. Therefore, hypoglycemic agents with more efficiency, less side effects, lower price and beneficial on liver- or kidney-disfunctioned patients still have necessity in the international medicinal market.

Although there are various natural plant extracts in the market announced to loss weight or reduce blood glucose, the scientific evidences are absent and these extracts cannot be acceptable by the clinical doctors and the international market. Accordingly, the purposes of the present invention is to overcome the drawbacks in the conventional extraction method, efficiently prepare the extracts on anti-diabetes and anti-metabolic diseases.

It is therefore attempted by the applicant to deal with the above situation encountered in the prior art.

SUMMARY OF THE INVENTION

For overcoming the drawbacks in the conventional extraction method and preparing the extracts on treatments of diabetes and metabolic diseases, the present invention uses the supercritical fluid technique to extract the leaves of *T. sinensis* to obtain the supercritical *T. sinensis* extract. The supercritical extract of *T. sinensis* can efficiently improve glucose absorption in vivo, improve lipid degradation, inhibit the formation of huge lipid droplet and improve metabolic syndromes, and thus can be prepared as food supplement and pharmaceuticals.

Supercritical fluid extraction (SFE) is a method commonly used for the separation of active compounds from herbs and natural products (Michielin et al., 2009). Supercritical carbon dioxide fluid (SCF), by its non-polarity, is effective in obtaining non-polar components (Yamaguchi et al., 1986). Supercritical carbon dioxide (sc-$CO_2$) is the most recognized supercritical solvent and is classified as GRAS (Generally Recognized as Safe) by the Food and Drug Administration of the United States. Carbon dioxide achieves the critical point of gas phase and liquid phase at 31.7° C. and 72.8 atm. However, at the conditions behind the critical temperature, critical pressure and critical density, $CO_2$ represents high solubility and high permeation owned by the supercritical fluids (Wang et al., 2009). Since materials can be extracted by $CO_2$ at normal temperature and $CO_2$ does not chemically react with the extracted materials, the materials still maintain their activity after extraction. Furthermore, $CO_2$ evaporates at normal temperature and pressure (NTP) after extraction, and thus the fast concentration effect of material can be achieved and the problem of the remaining solvent is absent. Thus, supercritical fluid has the effects on distillation and organic solvent extraction, and the separation effect of the raw material is achieved by the high diffusion coefficient, low viscosity, low surface tension of the supercritical fluid and the density adjustment. The use of sc-$CO_2$ as "green" solvents for chemical reactions and separations is currently an active research area (Wang et al., 2009). Sc-$CO_2$, characterized by its non-polarity, is effective in obtaining non-polar components (Yamaguchi et al., 1986) and is an attractive alternative of organic solvents due to its nonexplosivity, nontoxicity, chemical inertness, and low cost (Wang & Weller et al., 2008). In addition to the supercritical $CO_2$ fluid, other supercritical fluids can be applied in the present invention.

The first aspect of the present invention is to provide a preparation method of a *T. sinensis* extract for reducing a blood glucose level, including steps of: drying leaves of *T. sinensis*; pulverizing the leaf as particles; and extracting the particles with a supercritical carbon dioxide to obtain the *T. sinensis* extract. The leaf includes young leaves, matured leaves and/or young shoots.

The second aspect of the present invention is to provide a *T. sinensis* extract for reducing blood glucose level including at least one of a monoterpene, a monoterpene derivative, a diterpene derivative, a triterpene, a sesquiterpene, sequiterpene derivative, a saturated fatty acid, a unsaturated fatty acid, an alkane, an alkene and a phytosterol.

The monoterpene includes α-pinene and β-pinene, the monoterpene derivative includes limonene, the diterpene derivative includes phytol, and the triterpene includes squalene. The sesquiterpene includes α-cubebene, copaene, aromadendrene, caryophyllene, α-caryophyllene, β-caryophyllene, aristolene, γ-patchoulene, α-selinene, β-selinene, γ-selinene, elixnen, germacrene A, germacrene B, germacrene D, β-elemene, γ-elemene, δ-elemene, τ-elemene, γ-cadiene, τ-muurolene, α-farnesene and lepidozene, and the sesquiterpene derivative includes caryophylene oxide, spathulenol, ledene oxide, germacrene D-4-ol and globulol. The saturated fatty acid includes ethyl pentadecanoate and ethyl palmitate, and the unsaturated fatty acid includes methyl linoleate, ethyl 9,12-octadecadienoate and ethyl α-linolenate.

Alkane has a carbon number not less than 21, in particular, alkane includes n-heneicosane, n-docosane, n-tricosane, n-pentacosane, n-heptacosane, n-octacosane, n-nonacosane, n-hentriacontane, n-dotriacontane, n-pentatriacontane, n-hexatricontane, n-tritetracontane and n-tetratetracontane. The alkene includes (17E)-17-pentatriacontene, and the phytosterol includes β-sitosterol. The *T. sinensis* extract further includes 6-methyl-5-hepten-2-one and phytone.

The *T. sinensis* extract is manufactured as food and/or drugs, and further is used for improving metabolic diseases and inhibiting an accumulation of fats in the body.

The third aspect of the present invention is to provide a preparation method of a *T. sinensis* extract for reducing blood glucose level, including a step of extracting *T. sinensis* with a supercritical fluid to obtain the *T. sinensis* extract.

The supercritical fluid includes $CO_2$ supercritical fluid, and the *T. sinensis* extract further contains a *T. sinensis* essential oil. The leaf particles are obtained by sequentially drying and pulverizing the leaf.

The fourth aspect of the present invention is to provide a method for detecting at least one component in a *T. sinensis* extract, including a step of determining an amount of the at least one component using GC-MS, and the at least one component contains several groups of chemicals, as well as 6-methyl-5-hepten-2-one and phytone in the above-mentioned second aspect of the invention.

Since there does not have any reference to report the low-polarity material of *T. sinensis* to own the therapeutic effect of reducing blood glucose and inhibiting fat accumulation, the supercritical fluid extract of *T. sinensis* made by $CO_2$ supercritical fluid in the present invention is benefit for improving metabolic syndromes, and the extract can overcome the drawbacks in the prior art and thus has industrial usefulness.

The above objectives and advantages of the present invention will become more readily apparent to those ordinarily skilled in the art after reviewing the following detailed descriptions and accompanying drawings.

BRIEF DESCRIPTION OF THE DRAWINGS

In FIGS. 3A to 3D, the data are presented as mean±SD from six independent experiments, and each sample was performed in duplicate for glucose concentration measurement. a, p<0.05 compared to control; b, p<0.01 compared to control; c, p<0.001 compared to control.

FIG. 4 depicts the quantification of lipid accumulation in 3TE-adipocyte in different treatments. The data are presented as mean±SD from six independent experiments, and each sample was performed in duplicate for glucose concentration measurement. a, p<0.05 compared to control; N.S., no significance compared to control.

In FIGS. 5A and 5B, the data are presented as mean±SD from six independent experiments, and each sample was performed in duplicate for glucose concentration measurement. a, p<0.05 compared to control; b, p<0.01 compared to control; c, p<0.001 compared to control.

FIGS. 6A and 6B shows (A) the blood glucose change and (B) the body weight change in mice. The feeding of a high-fat diet was started at day-14, and day 0 represented the day of the STZ injection (45 mg/kg). DM represented the group of high-fat-diet-fed mice with the STZ injection; DM+TS-SCF represented the group of high-fat-diet-fed mice with the STZ injection plus TS-SCF (150 mg/kg/day) treatment; DM+Rosig represented the group of high-fat-diet-fed mice with the STZ injection plus rosiglitazone maleate (150 μg/kg/day). Data are mean±SD. a, p<0.001 compared to the control, DM+TS-SCF, or DM+Rosig groups.

DETAILED DESCRIPTION OF THE PREFERRED EMBODIMENT

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

Example 1: Supercritical Fluid Extraction for the Leaves of *T. sinensis* (TSL)

In order to perform a more extensive phytochemical screening and search for novel active compounds of leaves of *Toona sinensis*, supercritical fluid extraction (SFE) was used to obtain the non-polar constituents of TSL.

Figure 1:
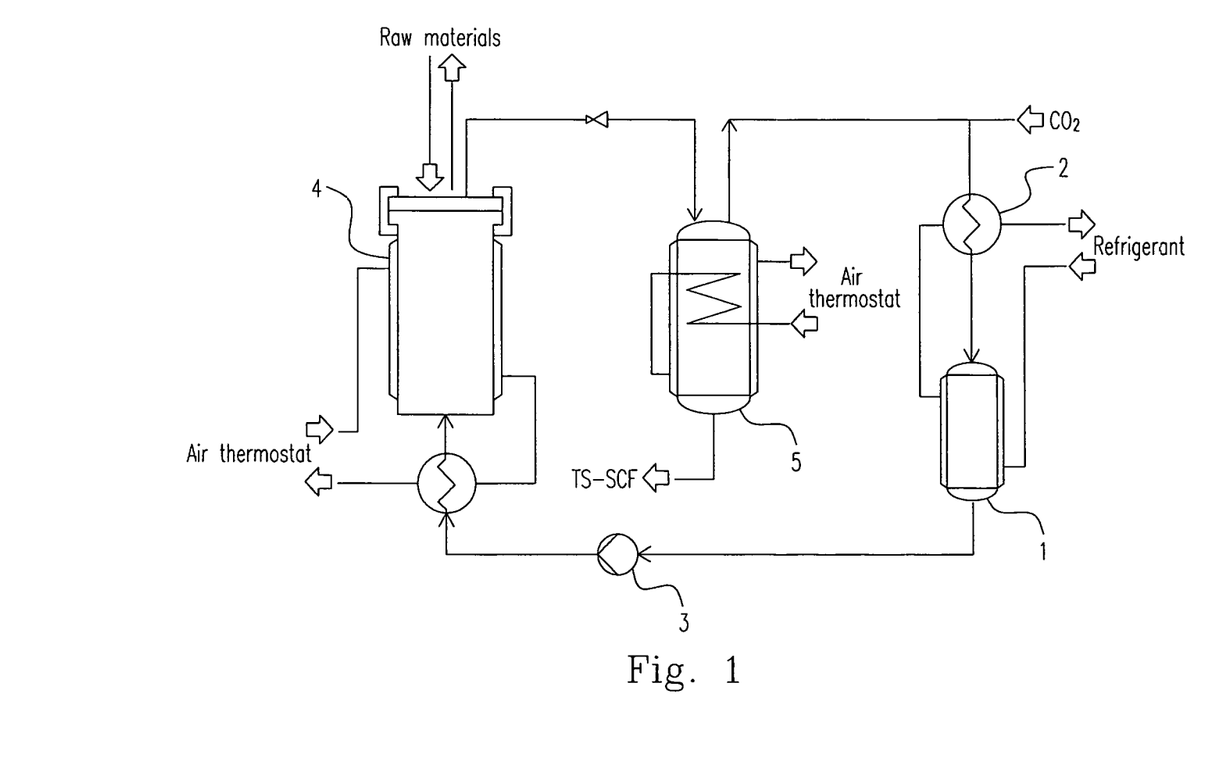
FIG. 1 depicts the schema showing the $CO_2$ supercritical fluid extractor for the *T. sinensis* supercritical extract in the present invention.

Method:

The raw material, "the leaves of *T. sinensis* (TSLs)", was pretreated for extraction with a cold-air-dried method and ground into 1~5-mm particles with a moisture content lower than 30%. To prepare the non-polar TSL extract, a pre-engineered supercritical fluid extraction pilot plant (Fa. NATEX Process Technology GmbH, Ternitz, Austria; extraction pressure up to 1000 bar and utilizable extraction volume at 5 L) was constructed. The extraction method and equipment were modified from the report of Roñyai et al., 1998. The scheme of the extraction procedure is shown in FIG. 1. A total of 1600 g of TSL was weighed accurately and supplied into the extraction vessel 4 for the extraction of solids. The extraction vessel was pressurized. Then, liquid $CO_2$ was flowed into the cooler 2 for precooling and was adjusted prior to the commencement of the extraction. Pure $CO_2$ was compressed by a high-pressure diaphragm pump 3 to 350-550 bar at 40-60° C. and allowed to flow through the extraction vessel at a flow rate of 30-35 kg $CO_2$ per hour. Supercritical-$CO_2$ is a solvent that is mainly suitable for transporting non-polar or weak-polar substances (TS-SCF) into the separator 5, where it is expanded by valves. After separation, the regenerated $CO_2$ flows back into the reservoir 1 and can be used for extraction again. The extraction time was in the range of 60 to 120 min, and the extraction was stopped depending on whether the yield was less than 0.1% of the TSL as 30-70 kg $CO_2$ passed through the vessel 4. To confirm the efficacy of supercritical-flow extracted leaves of *T. sinensis* from different resources (geographical or seasonal variation), three different batches of TSLs were collected and extracted using the method mentioned above. After the manufacturing processes, three extracts were harvested and named TS-SCF-I, TS-SCF-II and TS-SCF-III, respectively.

Result:

Each batches of supercritical-$CO_2$ fluid extract of TSL was obtained from the separator 5 and processed an water-drying procedure, and the recovery was 14%~18%. The raw material of EXAMPLE 1 included the young shoots, young leaves and matured leaves of *T. sinensis*.

Example 2: GC/MS Analyses of TS-SCF

Method:

Chemical constituents of TS-SCF were analyzed by gas chromatography-mass spectrometry (DSQ II Single Quadrupole GC/MS, Thermofisher Scientific, USA) on a 30 m×0.25 mm×0.25 μm DB-5MS capillary column (Agilent J&W Scientific). The column oven temperature was programmed as follows: 100° C. (5 min) to 119° C. at 40° C./min, maintained at 119° C. for 26 min, then to 157° C. at 8° C./min, maintained at 157° C. for 5 min, then to 181° C. at 40° C./min, immediately heated to 188° C. at 3° C./min, held for 23 min, then increased to 230° C. at 5° C./min, held for 10 min, then raised to 242° C. at 5° C./min, held for 5 min, then heated to 280° C. at 1° C./min, and held for 10 min. The other parameters were as follows: injection temperature, 250° C.; ion source temperature, 250° C.; EI (electron bomb ionization), 70 eV; carrier gas, He at 1 mL/min; injection volume, 5 μL; split ratio, 1:50; and mass range, m/z 45-800. Identification of the compounds was based on a comparison of retention indices (determined relative to the retention times of n-alkanes on the DB-5MS column) and mass spectra with those of authentic samples, data from Wiley/NBS Registry of Mass Spectral Data (V. 5.0)/National Institute of Standards and Technology (NIST) MS Search V. 2.0 and the literature. The relative percentage of each compound in TS-SCF was quantified based on the peak area integrated by the analysis program.

Figure 2A:
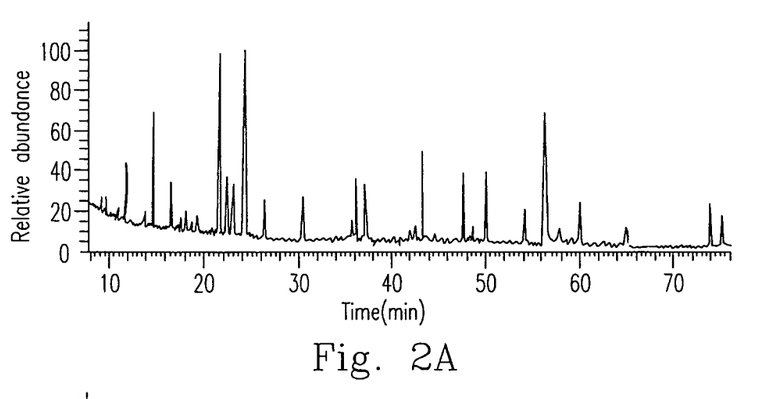
FIGS. 2A to 2B depicts the diagram of the non-polar constituents of *T. sinensis* extract analyzed by GC/MS.
Figure 2B:
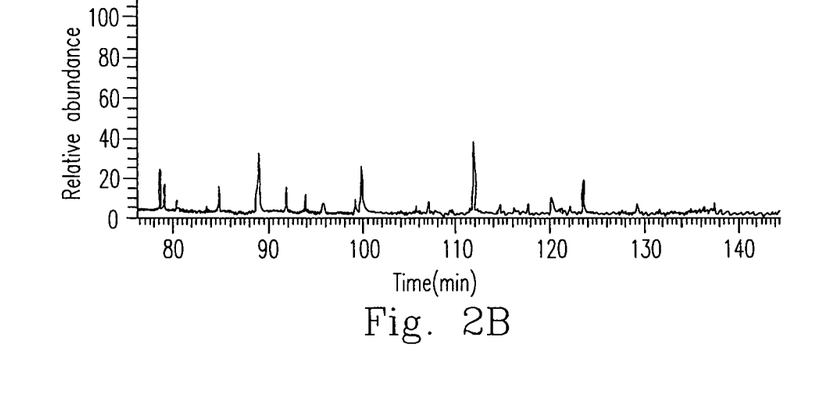

Result:

The yield of supercritical-$CO_2$ extraction from TSLs was 14-18% (w/w) according to the 30% dry weight of raw material. Taking TS-SCF for example, a total of 24 main constituents of TS-SCF were identified as shown in Table 1, and the chemical profile was presented in FIGS. 2A and 2B. Most of the constituents in the TS-SCF extract can be classified into different chemotypes, including monoterpenes and its derivatives, sesquiterpenes and its derivatives, saturated and unsaturated fatty acids, long-chain n-alkenes, phytosterols and others. The components of another three batches was listed in Table 1. Since different batches of TS-SCF were made from *T. sinensis* planted in different areas in Taiwan, the above-mentioned compounds would not appear in each batch of TS-SCF.

TABLE 1

Total vision of components from every batch of TSLs

| Components (TS-SCF-I) | $Ki^a$ | Components (TS-SCF-II) | $Ki^a$ | Components (TS-SCF-III) | $Ki^a$ | Components (TS-SCF) | $Ki^a$ |
|---|---|---|---|---|---|---|---|
| Monoterpenes | | Monoterpenes | | Sesquiterpenes | | Sesquiterpenes | |
| α-Pinene | 938 | α-Pinene | 936 | Elixene | 1199 | δ-Elemene | 1340 |
| β-Pinene | 982 | Sesquiterpenes | | δ-Elemene | 1341 | β-Elemene | 1386 |
| Monoterpene derivatives | | β-Elemene | 1386 | Copaene | 1398 | β-Caryophyllene | 1417 |
| Limonene | 1026 | Copaene | 1389 | β-caryophyllene | 1416 | Germacrene D | 1481 |
| Sesquiterpenes | | γ-Elemene | 1437 | γ-Patchoulene | 1441 | α-Selinene | 1489 |
| α-Cubebene | 1355 | τ-Muurolene | 1468 | α-Caryophyllene | 1453 | γ-Selinene | 1497 |
| β-Elemene | 1389 | β-Selinene | 1483 | Germacrene D | 1483 | Germacrene A | 1508 |
| Copaene | 1396 | α-Selinene | 1489 | β-Selinene | 1485 | α-Farnesene | 1512 |

TABLE 1-continued

Total vision of components from every batch of TSLs

| Components (TS-SCF-I) | Ki[a] | Components (TS-SCF-II) | Ki[a] | Components (TS-SCF-III) | Ki[a] | Components (TS-SCF) | Ki[a] |
|---|---|---|---|---|---|---|---|
| Caryophyllene | 1467 | Aromadendrene | 1753 | γ-Selinene | 1497 | Lepidozene | 1528 |
| Germacrene D | 1481 | Sesquiterpene derivatives | | Germacrene A | 1510 | Germacrene B | 1563 |
| β-Selinene | 1486 | Caryophylene oxide | 1567 | Germacrene B | 1563 | Sesquiterpene derivatives | |
| τ-Elemene | 1488 | Spathulenol | 1574 | Aristolene | 1756 | Germacrene D-4-ol | 1574 |
| Germacrene A | 1506 | Ledene oxide | 1892 | Aromadendrene | 1758 | Spathulenol | 1576 |
| Germacrene B | 1561 | Diterpene derivatives | | long-chain n-alkanes | | Globulol | 1578 |
| γ-Cadiene | 1752 | Phytol | 1949 | n-Heneicosane | 2102 | Diterpene derivatives | |
| Saturated fatty acids | | Saturated fatty acids | | n-Docosane | 2201 | Phytol | 1949 |
| Ethyl pentadecanoate | | Ethyl pentadecanoate | 1997 | n-Tricosane | 2308 | Saturated fatty acids | |
| Unsaturated fatty acids | | Unsaturated fatty acids | | n-Octacosane | 2804 | Ethyl palmitate | 1975 |
| Methyl linoleate | | Methyl linoleate | 2091 | n-Hentriacontane | 3000 | Unsaturated fatty acids | |
| | | Long-chain n-alkanes | | n-Dotriacontane | 3201 | Ethyl 9,12-octadecadienoate | 2173 |
| | | n-Heptacosane | 2703 | n-Pentatriacontane | 3503 | Ethyl α-linolenate | 2176 |
| | | n-Octacosane | 2804 | n-Hexatricontane | 3601 | Long-chain n-alkanes | |
| | | n-Pentatriacontane | 3500 | n-Tritetracontane | 4305 | n-Pentacosane | 2500 |
| | | n-tetratetracontane | 4402 | n-Tetratetracontane | 4400 | n-Heptacosane | 2700 |
| | | Alkenes | | | | n-Nonacosane | 2900 |
| | | (17E)-17-Pentatriacontene | 3499 | | | n-Hentriacontane | 3100 |
| | | Others | | | | n-Pentatriacontane | 3500 |
| | | 6-methyl-5-hepten-2-one | 984 | | | Triterpene | |
| | | Phytone | 1850 | | | Squalene | 2790 |
| | | | | | | Phytosterols | |
| | | | | | | β-Sitosterol | 3410 |

[a]Kovats index relative to n-alkanes (C10-C40) on DB-5MS column and the identification was based on comparison of the mass spectrum from database, Kovats index on a DB-5MS column in reference.

Example 3: In Vitro Model for Determination of Anti-Diabetic Effect

Adipose tissue is one of the major sites of postprandial glucose uptake (Watson et al., 2007). To speed up the screening of novel anti-diabetic candidate materials from natural products, an in vitro model was established by comparing the 24-hour glucose consumption from the culture medium of 3T3-L1 adipocytes.

Method:

The same amount ($5 \times 10^5$ cells) of 3T3-L1 preadipocytes (BCRC #60159; Bioresource Collection and Research Center, Taiwan) was seeded and cultured in normal glucose (100 mg/dL) DMEM supplemented with 10% FBS, 100 U/mL of penicillin, and 100 μg/mL of streptomycin in a humidified atmosphere of 95% air and 5% $CO_2$ at 37° C. When the cell density reached 100% confluence, 3T3-L1 preadipocytes were induced to differentiate by treating the culture with 450 mg/dL D-glucose, 0.32 μM insulin, 0.5 mM 3-isobutyl-1-methylxanthine and 1 μM dexamethasone for two days. Then, the culture medium of the differentiated adipocytes was changed to DMEM containing 300 mg/dL D-glucose with or without the administration of TSL extracts. After 24 hours, the anti-diabetic activity was determined by measuring the medium glucose concentration using a Roche Cobas Integra 400 Chemistry Analyzer (Roche Diagnostics, Taipei, Taiwan). The coefficient of variation (CV) of the analyzer was 0.62-0.92% within-run and 1.1-1.2% between days. To confirm whether the in vitro model was sufficient to measure the glucose-lowering effect, insulin and rosiglitazone were used as positive controls.

Figure 3A:
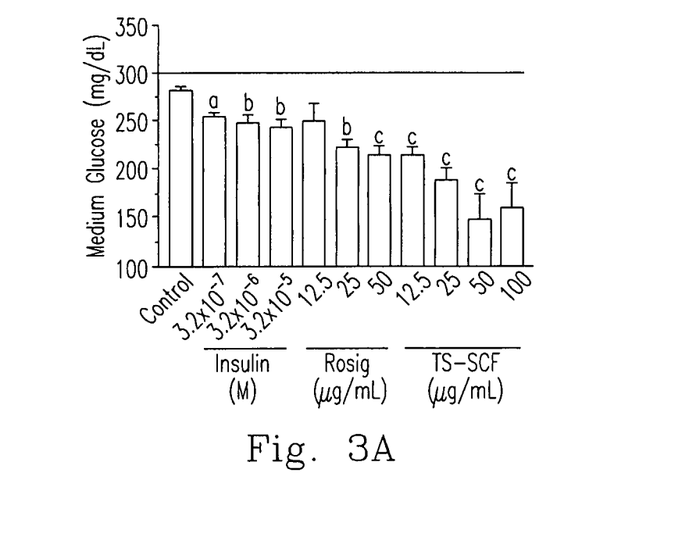
FIG. 3A shows the remaining glucose concentrations of the media consumed by the differentiated 3T3-L1 cells by the treatment without (control) or with insulin, rosiglitazone or TS-SCF.
Figure 3B:
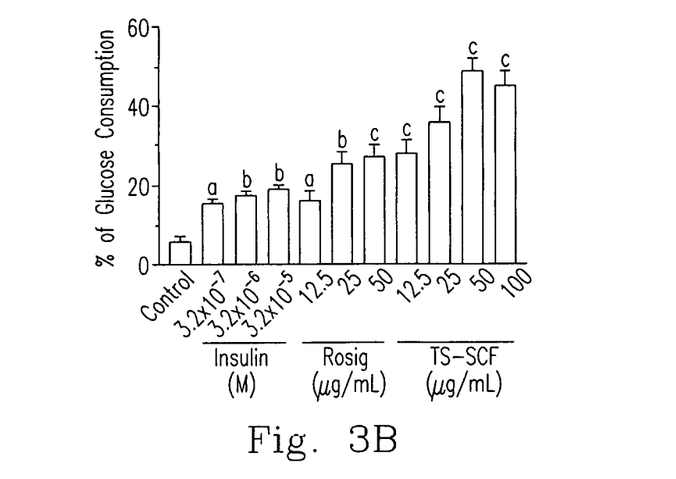
FIG. 3B shows the percentages of glucose consumed by 3T3-L1 adipocytes with a started concentration of 300 mg/dL.
Figure 3C:
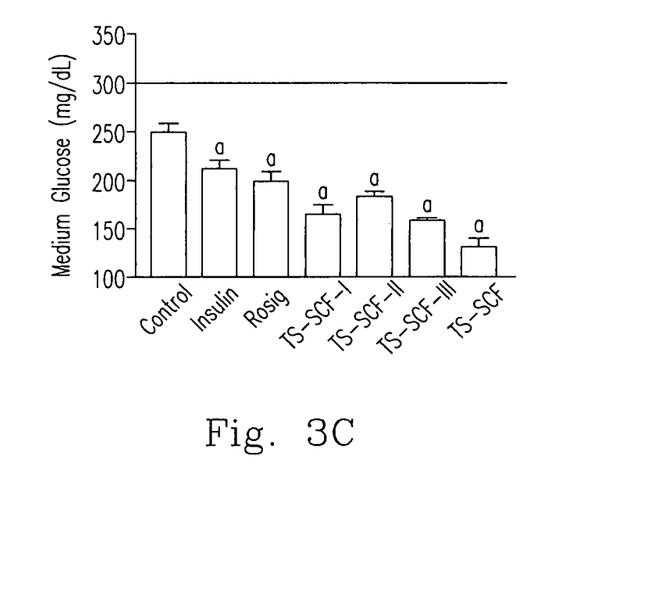
FIGS. 3C and 3D show the comparison of (C) the medium glucose and (D) the percentage of glucose consumption among the batches of TS-SCFs.
Figure 3D:
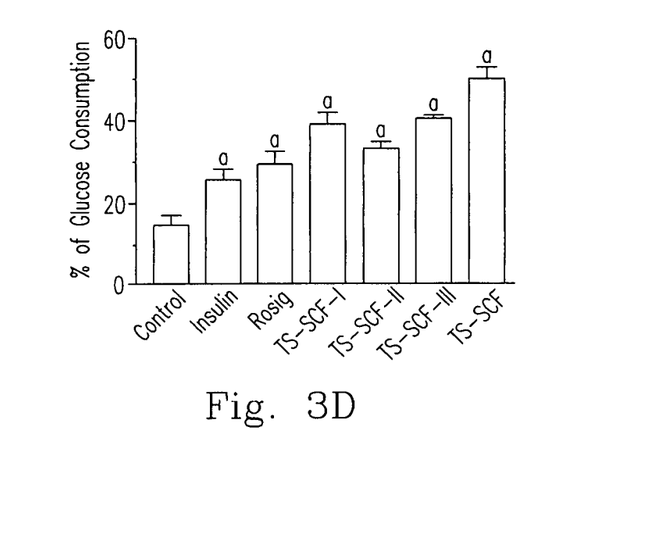

Result:

As shown in FIG. 3A, the medium glucose concentration was decreased by approximately 18 mg/dL in the control group without the addition of any anti-diabetic reagent after 24 hours, with a starting glucose concentration of 300 mg/dL. When converted to the percentage of glucose consumption, only about 6% of the glucose in the medium was used by 3T3-L1 adipocytes (FIG. 3B). Insulin (i.e., $3.2 \times 10^{-7}$ to $3.2 \times 10^{-5}$ M) decreased by approximately 46-57 mg/dL, and rosiglitazone (abbreviated as "Rosig", i.e., 12.5 to 50 μg/mL) decreased by approximately 50-80 mg/dL of the glucose concentration in the media (FIG. 3A). By converting the data to percentage of glucose consumption, insulin and rosiglitazone increased the use of medium glucose to 15-18% and 16-27%, respectively (FIG. 3B). Compared to the control group, insulin and rosiglitazone significantly decreased the glucose concentrations of the media in a dose-dependent manner in the 3T3-L1 adipocyte model, indicating that this in vitro model could be used as a quick screening method for novel anti-diabetic reagents that target adipocytes. Through this in vitro model, it was observed that TS-SCF possessed an excellent anti-diabetic effect. The glucose-lowering effect of 12.5 μg/mL of TS-SCF was equal to that of 50 μg/mL of rosiglitazone (FIG. 3A). A total of 50 μg/mL of TS-SCF could increase the use of medium glucose to approximate 50% (FIG. 3B). As shown in FIGS. 3C and 3D, the administration of every batch of TS-SCF (50 μg/mL) could significantly decreased the glucose concentrations of the media and possessed an excellent anti-diabetic effect in our 3T3-L1 adipocyte model.

Example 4: TS-SCF Blocked Adipogenesis in Adipocytes

Method:

Lipid droplets were detected by Oil Red O staining (Kinkel et al., 2004). 3T3-L1 cells were washed three times with PBS and fixed in 10% formalin for 1 hour. After washing with PBS, the cells were stained with Oil Red O staining solution (0.5% Oil Red O in 100% propylene glycol). After 1 hour, cells were washed three times with water and observed under a phase contrast microscope. To quantify the cellular lipid quantity, stained cells were incubated with 100% isopropanol and shaken at room temperature for 20 minutes, and then Oil Red O in the supernatant was measured at 490 nm by an ELISA reader.

Figure 4:
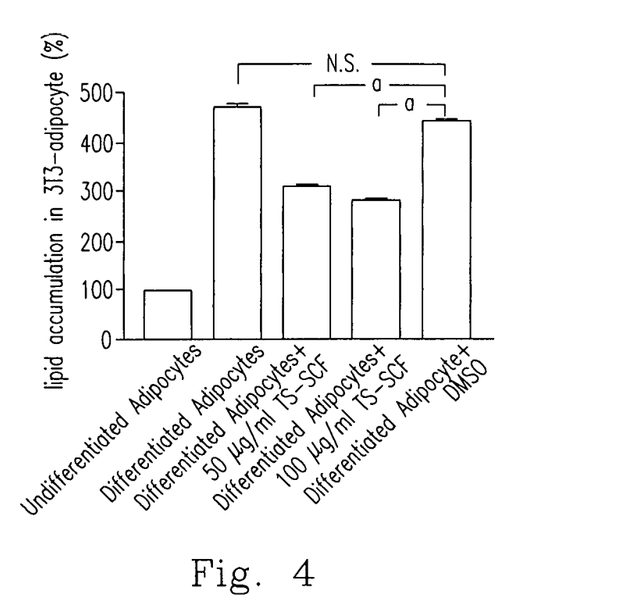

Result:

On day 6, a significant increase in lipid droplet formation was observed by Oil Red O staining in the differentiated cells relative to the undifferentiated cells. The formation of lipid droplets was almost completely blocked when TS-SCF was added to the induction medium, the DMSO treated group was blank (data not shown). After extracting the Oil Red O from the cells, a serious increase in lipid accumulation was observed in the differentiated group (FIG. 4). In contrast, induced cells that were co-treated with 50, 100 µg/mL TS-SCF showed significant increases in lipid formation, as compared to the undifferentiated group (FIG. 4). These results indicate that inhibition of TS-SCF obstructed adipogenesis in adipocytes.

Example 5: Anti-Diabetic Effect of Extracts of High to Mid/High Polar Components of TSL Differed from TSL-SCF As the described above, supercritical fluid extract of TSL (TS-SCF) exhibited hypoglycemia effect and inhibitory action of lipid accumulation during differentiation of 3T3-L1 preadipocytes, and the components was identified as non-polar compositions in the present invention. To compare with the prior art that mentioned the effective chemical components of TSL extracts have so far shown a distribution in the range from high to mid-high polarity (e.g., aqueous extract, aqueous solution processed by using 99.5% to 25% of ethanol, methanol extract, and aqueous extract of fermented *Toona sinensis*), three different extraction methods were generalized to confirm the anti-diabetic effect of the extracts, respectively.

Method:

The methods of in vitro model for determination of anti-diabetic effect are the same as the contents described in EXAMPLE 3. To obtain the high to mid-high polar components of TSL, three different extraction methods were used to produce the following extracts, which were previously reported (Liao et al., 2007; Hsieh et al., 2005; Yang et al., 2003). TSLs were (i) extracted by reverse-osmosis of water (1:4 w/v) by boiling for 30 min and then cooling down without further boiling for two hours at room temperature (Liao et al., 2007); (ii) extracted by soaking in 100° C. boiled water (1:10 w/v) three times, each time for 30 min (Hsieh et al., 2005); and (iii) extracted by boiling in 50% v/v alcohol/water for three hours (Yang et al., 2003). Next, the leaves were removed and the remaining liquids were filtered through filter paper (Advantec, Tokyo, Japan). Afterward, the filtrated solutions were concentrated using an evaporator (rotary vacuum evaporator, vv2000; Heidolph, Schwabach, Germany) under reduced pressure and three crude extracts were obtained, which were named TS-WB (i), TS-WS (ii), and TS-E (iii); the yield of each extract was 6.03%, 5.13%, and 8.36%, respectively.

Figure 5A:
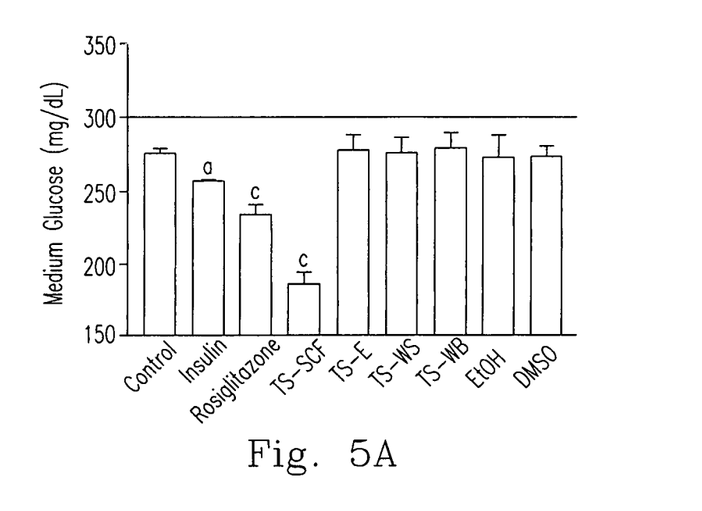
FIGS. 5A and 5B are the drawings showing the effects of insulin, rosiglitazone (Rosig), and TSL extracts on (A) the medium glucose and (B) the glucose consumption in 3T3-L1 adipocyte model.
Figure 5B:
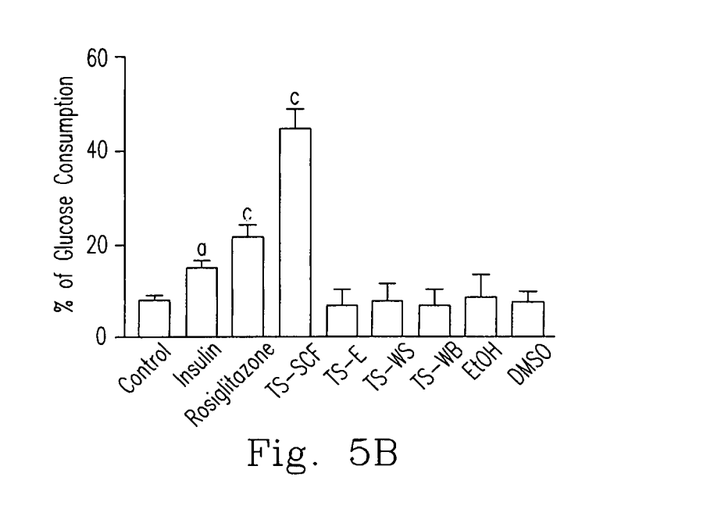

Result:

FIGS. 5A and 5B show the comparison of glucose-lowering effects among the non-polar TSL extract (i.e., TS-SCF) and the high to mid-high polar TSL extracts (i.e., TS-E, TS-WS, and TS-WB). The results demonstrate that only the TS-SCF significantly reduced the glucose in the media after the adipocytes were treated with an equal concentration (i.e., 50 µg/mL) of each TSL extract for 24 hours (FIG. 5A). Equal volume of solvents (100% EtOH or 100% DMSO) that were used to dissolve the reagents showed no influence on medium glucose consumption in 3T3-L1 adipocytes. FIG. 5B shows the data converted to the percentage of glucose consumption.

Example 6: Determination of Anti-Diabetic Effect In Vivo

Method:

Eight-week-old male C57BL/6J mice were obtained from BioLASCO Technology (Charles River Taiwan Ltd.). All of the mice received standard animal care under supervision of the Institutional Animal Care and Use Committee of Kaohsiung Medical University, Taiwan. The mice were caged in an air-conditioned animal facility at 23° C. on a 12-h light/dark cycle and were maintained with free access to water and food. Animals were fed either a normal chow diet consisting (as a percentage of total kcal) of 11% fat, 65% carbohydrate, and 24% protein (Maintenance diet 1320, Altromin Spezialfutter GmbH & Co. KG, Germany) or a high-fat diet consisting of 45% fat, 35% carbohydrate, and 20% protein (D12451, Research Diets, Inc., New Brunswick, N.J., USA). After two weeks on either diet, mice were divided into four groups: (i) control (n=7); (ii) high-fat-diet mice with STZ injection (DM; n=5); (iii) high-fat-diet mice with STZ injection plus TS-SCF treatment (DM+TS-SCF; n=6); and (iv) high-fat-diet mice with STZ injection plus rosiglitazone treatment (DM+Rosig; n=4). The mice in groups ii-iv were injected with STZ (45 mg/kg), and both STZ-injected and non-injected animals were kept on their original diets (chow or high-fat) for the duration of the study. TS-SCF (150 mg/kg/day) and rosiglitazone (150 µg/kg/day) treatments via gastric gavage were begun two days after the STZ injection. The rosiglitazone maleate used in this experiment did not contain any inactive ingredient and the pure compound was kindly provided by GlaxoSmithKline, Ltd. (Taiwan).

Throughout the experiment, body weight and blood glucose from the tail tip were monitored weekly. Blood glucose was detected by the ACCU-CHEK blood glucose meter (Roche Diagnostics, Taipei, Taiwan). Animals were sacrificed after eight weeks of STZ injection and were euthanized by intraperitoneal injection with the anesthetic Zoletil (10 mg/kg) (Virbac, Carros, France). Blood samples were collected from the heart at the time of sacrifice for the measurement of biochemistry data using a Roche Cobas Integra 400 Chemistry Analyzer (Roche Diagnostics, Taipei, Taiwan).

Insulin from plasma were detected by ELISA kits (Crystal Chem, Inc. Downers Grove, USA). The homeostasis model assessment of insulin resistance (HOMA-IR) was calculated using the following formula: fasting blood glucose (mg/dL)×fasting insulin (µU/mL)/405.

Figure 6A:
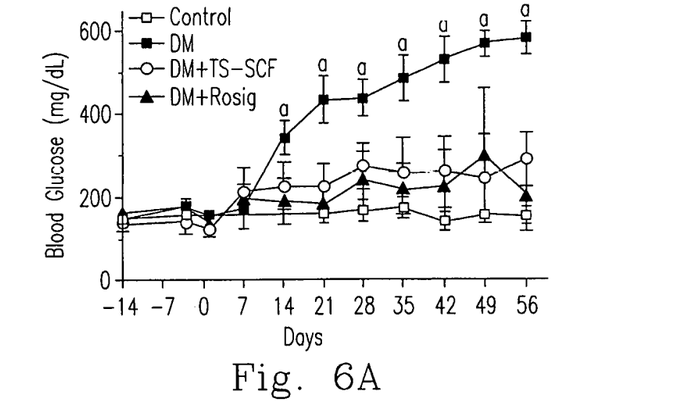
Figure 6B:
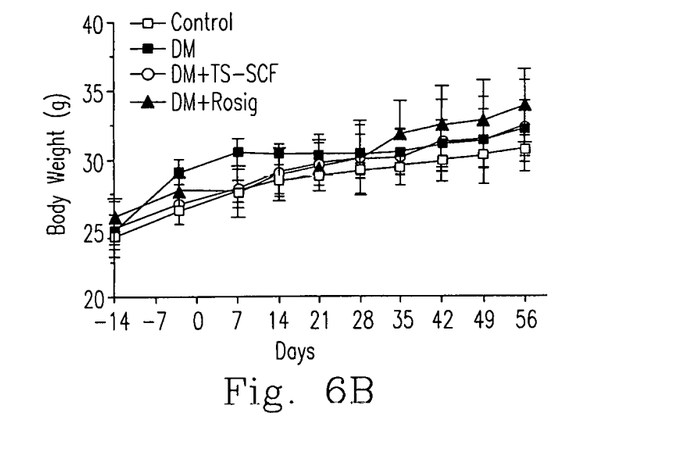

Result:

After the evaluation of glucose-lowering potential via our in vitro model, the anti-diabetic effect of TS-SCF was further confirmed by the type 2 diabetic mouse model. FIG. 6A shows that the blood glucose significantly increased 14 days after the low-dose STZ injection in the DM group compared to that of the control group, the DM with TS-SCF-treated group, or the DM with rosiglitazone-treated group. The blood glucose level continuously increased to 584.60±87.65 mg/dL 56 days after the injection with STZ. In contrast, TS-SCF and rosiglitazone significantly prevented the progression of diabetes and controlled the glucose level between 200 and 300 mg/dL during the experimental period (FIG. 6A). FIG. 6B shows that there was no significant difference in the body weight change among these four groups.

Table 2 summarizes the biochemical data of the mice. There was no significant difference in the gains in body weight among the four groups (p=0.7122). Relative to the control group, the fasting plasma glucose significantly increased in the DM group (p<0.001). In comparison with the DM group, the TS-SCF and the rosiglitazone groups showed significantly lower fasting glucose levels (Table 2). The fasting plasma insulin levels showed no significant difference among the groups (p=0.1688). However, the HOMA-IR (homeostasis model assessment for insulin resistance) was significantly higher in the DM group (p<0.001 compared to the control group). The treatments of TS-SCF and rosiglitazone showed to have notably lower HOMA-IR values (p<0.001 compared to the DM group), indicating that TS-SCF and rosiglitazone could maintain insulin sensitivity in the mice. In addition to preventing the progression of diabetes, TS-SCF, as with rosiglitazone, significantly decreased the plasma triglycerol level, which was elevated in the DM group (Table 2). However, TS-SCF and rosiglitazone reduce the total plasma cholesterol level was not observed (Table 2). The plasma ALT level was increased in the DM group; in contrast, TS-SCF significantly prevented the elevation of plasma ALT levels (Table 2). Compared to the control group, the plasma levels of ALT and creatinine were not elevated by the TS-SCF treatment, indicating that TS-SCF had no hepatic or renal toxicity throughout the eight-week administration.

Result:

The cell size of adipocytes in the DM group was enlarged compared to that of the control group. Relative to the DM group, administration of TS-SCF could reduce the cell size. In contrast, the rosiglitazone treatment maintained cell sizes as large as those of the DM group. The hepatosteatosis in the DM mice was characterized by ballooned hepatocytes. The administration of TS-SCF and rosiglitazone could effectively prevent the hepatosteatosis.

Example 8: Effect of TS-SCF on Adiponectin and TNF-α Production in type 2 Diabetic Mouse Model Adiponectin is a protective adipokine that has anti-inflammatory and anti-atherosclerotic effects; a deficiency of adiponectin has been associated with obesity-related disorders such as diabetes and cardiovascular disease (Kiess et al., 2008). TNF-α, a proinflammatory cytokine, is expressed in and secreted by adipose tissue, its levels correlating with the degree of adiposity and associated insulin resistance. Targeting TNF-α and/or its receptors has been suggested as a promising treatment for insulin resistance and type 2 diabetes (Chen et al., 2010).

Method:

Adiponectin, and TNF-α from plasma were detected by ELISA kits (MyBioSource, LLC, San Diego, USA).

TABLE 2

Biochemical data of mice.

| | Control | DM | DM + TS-SCF | DM + Rosiglitazone | p-value |
|---|---|---|---|---|---|
| Body weight gain (g) | 6.70 ± 1.50 | 7.47 ± 1.77 | 7.52 ± 1.98 | 8.10 ± 1.95 | 0.7122 |
| Fasting glucose (mg/dL) | 155.14 ± 21.30 | 484.60 ± 87.65$^a$ | 290.00 ± 65.55$^b$ | 205.00 ± 84.87$^b$ | 0.0001 |
| Insulin (ng/mL) | 1.45 ± 0.76 | 1.31 ± 0.71 | 0.66 ± 0.51 | 0.98 ± 0.77 | 0.1688 |
| HOMA-IR | 15.92 ± 1.15 | 44.83 ± 4.39$^a$ | 13.47 ± 2.38$^b$ | 14.29 ± 4.60$^b$ | 0.0001 |
| Triglycerol (mg/dL) | 72.87 ± 13.70 | 94.42 ± 16.70$^c$ | 63.27 ± 5.34$^d$ | 64.94 ± 4.82$^d$ | 0.0017 |
| T-CHO (mg/dL) | 87.32 ± 6.57 | 130.01 ± 10.60$^a$ | 138.68 ± 16.00 | 137.65 ± 32.62 | 0.0001 |
| HDL-C (mg/dL) | 76.23 ± 6.87 | 110.72 ± 7.91$^a$ | 125.95 ± 9.19$^e$ | 126.03 ± 32.17 | 0.0001 |
| LDL-C (mg/dL) | 5.25 ± 3.21 | 10.21 ± 0.96$^f$ | 8.03 ± 1.14 | 9.81 ± 8.29 | 0.1576 |
| ALT (U/L) | 39.76 ± 7.17 | 50.62 ± 8.13$^f$ | 38.30 ± 6.86$^e$ | 62.00 ± 27.00 | 0.0058 |
| Creatinine (mg/dL) | 0.48 ± 0.47 | 1.53 ± 0.64$^c$ | 0.71 ± 0.40$^e$ | 0.54 ± 0.18$^e$ | 0.0081 |

Values are mean ± SD, and data were analyzed by one-way analysis of variance and the Bonferroni test HOMA-IR: homeostasis model assessment for insulin resistance, T-CHO: total cholesterol, HDL-C: HDL cholesterol, LDL-C: LDL cholesterol, and ALT: alanine aminotransferase
$^a$p < 0.001 compared to control
$^b$p < 0.001 compared to DM
$^c$p < 0.05 compared to control
$^d$p < 0.01 compared to DM
$^e$p < 0.05 compared to DM
$^f$p < 0.01 compared to control Example 7: Morphological Evaluation of Adipose and Hepatic Tissues Method:

A sample of adipose and hepatic tissues from each mouse was fixed in 4% formaldehyde and embedded in paraffin wax. Sections were stained with hematoxylin and eosin (H&E) and observed using a microscope. The morphological evaluation of was performed by hematoxylin and eosin stains.

Figure 7A:
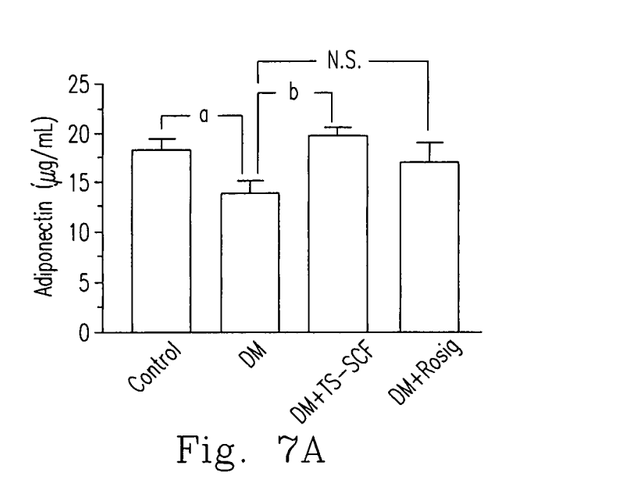
FIGS. 7A and 7B are the drawings showing the plasma levels of (A) adiponectin and (B) TNF-α both detected by ELISA kits. Data are mean±SD. a, p<0.05; b, p<0.01; N.S., no significance.
Figure 7B:
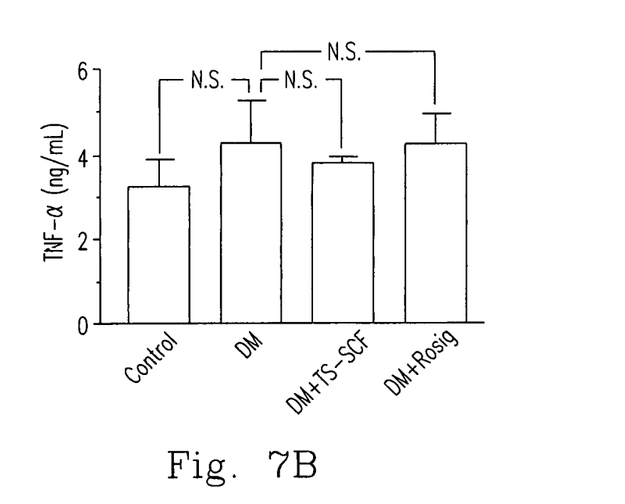

Result:

As shown in FIG. 7A, plasma adiponectin was decreased in the DM group relative to the control group (p<0.05). Treatment with TS-SCF could significantly reverse the decrease of plasma adiponectin (p<0.01 compared to the DM group). The plasma TNF-α level was not significantly increased in the DM group after our 8-week experimental period, and the values were not significantly different among the four groups (FIG. 7B).

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for treating a metabolic disease, comprising:
providing an effective amount of a pharmaceutical composition being a low-polarity *Toona sinensis* extract; and
administering the pharmaceutical composition to a subject in need thereof, wherein the pharmaceutical composition has at least one effectiveness of reducing a blood glucose level, inhibiting an accumulation of fats, improving metabolic syndromes, preventing hepatosteatosis, decreasing a plasma triglycerol level, lowering an insulin resistance and increasing a plasma adiponectin level, wherein the effective amount of the pharmaceutical composition is sufficient to provide a blood concentration from 12.5 µg/mL to 100 µg/mL in the subject.

2. The method according to claim 1, wherein the low-polarity *Toona sinensis* extract is one of a non-polar *Toona sinensis* extract and a weak-polar *Toona sinensis* extract.

3. The method according to claim 1, wherein the low-polarity *Toona sinensis* extract is extracted by a supercritical carbon dioxide.

4. The method according to claim 1, wherein the low-polarity *Toona sinensis* extract comprises at least one selected from a group consisting of a monoterpene, a monoterpene derivative, a diterpene derivative, a triterpene, a sesquiterpene, a sesquiterpene derivative, a saturated fatty acid, an unsaturated fatty acid, an alkane, an alkene and a phytosterol.

5. The method according to claim 4, wherein the sesquiterpene comprises at least one selected from a group consisting of an α-cubebene, a copaene, an aromadendrene, a caryophyllene, an α-caryophyllene, a β-caryophyllene, an aristolene, a γ-patchoulene, an α-selinene, a β-selinene, a γ-selinene, an elixnen, a germacrene A, a germacrene B, a germacrene D, a β-elemene, a γ-elemene, a δ-elemene, a τ-elemene, a γ-cadiene, a τ-muurolene, an α-farnesene and a lepidozene, and the sesquiterpene derivative comprises a caryophylene oxide, a spathulenol, a ledene oxide, a germacrene D-4-ol and a globulol.

6. The method according to claim 4, wherein the saturated fatty acid comprises at least one of an ethyl pentadecanoate and an ethyl palmitate, the unsaturated fatty acid comprises at least one selected from a group consisting of a methyl linoleate, an ethyl 9,12-octadecadienoate and an ethyl α-linolenate, and the alkane has a carbon number no less than 21.

7. The method according to claim 4, wherein the alkane comprises at least one selected from a group consisting of an n-heneicosane, an n-docosane, an n-tricosane, an n-pentacosane, an n-heptacosane, an n-octacosane, an n-nonacosane, an n-hentriacontane, an n-dotriacontane, an n-pentatriacontane, an n-hexatricontane, an n-tritetracontane and an n-tetratetracontane.

8. The method according to claim 4, wherein the alkene comprises a (17E)-17-pentatriacontene, and the phytosterol comprises a β-sitosterol.

9. The method according to claim 4, wherein the low-polarity *Toona sinensis* extract further comprises a 6-methyl-5-hepten-2-one and a phytone.

10. The method according to claim 1, wherein the pharmaceutical composition is manufactured as one of a food and a drug.

* * * * *